United States Patent
Ionasec

(10) Patent No.: US 11,170,499 B2
(45) Date of Patent: Nov. 9, 2021

(54) METHOD AND DEVICE FOR THE AUTOMATED EVALUATION OF AT LEAST ONE IMAGE DATA RECORD RECORDED WITH A MEDICAL IMAGE RECORDING DEVICE, COMPUTER PROGRAM AND ELECTRONICALLY READABLE DATA CARRIER

(71) Applicant: Siemens Healthcare GmbH, Erlangen (DE)

(72) Inventor: Razvan Ionasec, Nuremberg (DE)

(73) Assignee: SIEMENS HEALTHCARE. GMBH, Erlangen (DE)

( * ) Notice: Subject to any disclaimer, the term of this patent is extended or adjusted under 35 U.S.C. 154(b) by 132 days.

(21) Appl. No.: 16/196,443

(22) Filed: Nov. 20, 2018

(65) Prior Publication Data

US 2019/0164279 A1    May 30, 2019

(30) Foreign Application Priority Data

Nov. 28, 2017  (DE) .......................... 102017221297.7

(51) Int. Cl.
  *G06K 9/00*    (2006.01)
  *G06K 9/03*    (2006.01)
  (Continued)

(52) U.S. Cl.
  CPC ........ *G06T 7/0012* (2013.01); *G06K 9/00369* (2013.01); *G06N 20/00* (2019.01); *G16H 30/40* (2018.01); *G06K 2209/05* (2013.01); *G06T 2207/20081* (2013.01); *G06T 2207/20084* (2013.01); *G06T 2207/30168* (2013.01); *G06T 2207/30196* (2013.01)

(58) Field of Classification Search
  None
  See application file for complete search history.

(56) References Cited

U.S. PATENT DOCUMENTS 6,411,840 B1 *  6/2002  Bardy .................. A61B 5/0031
                                                        600/513
9,295,406 B2 *  3/2016  Zuehlsdorff ........... G16H 50/30
(Continued)

OTHER PUBLICATIONS

German Office Action for German Application No. 102017221297.7 dated Jul. 31, 2018.

*Primary Examiner* — Soo Shin
(74) *Attorney, Agent, or Firm* — Harness, Dickey & Pierce, P.L.C.

(57) ABSTRACT

A method is for the automated evaluation of at least one image data record of a patient recorded with a medical image recording device for the preparation of diagnostic findings. In the method, at least one item of input data describing the patient and/or the recording process and/or the examination target is determined after completion of the recording of the image data record. A selection algorithm which evaluates the image data record and the input data is used for determining at least one automated evaluation process to be applied and applicable and at least one image quality measure with regard to the evaluation process is determined by evaluating the image data record. The selected automated evaluation process is only performed for an image quality measure meeting a threshold quality requirement.

27 Claims, 2 Drawing Sheets

(51) Int. Cl.
*G06N 3/08* (2006.01)
*G06T 7/00* (2017.01)
*G16H 10/60* (2018.01)
*G16H 15/00* (2018.01)
*G16H 30/40* (2018.01)
*G16H 50/20* (2018.01)
*G16H 50/30* (2018.01)
*G06N 20/00* (2019.01)

(56) References Cited

U.S. PATENT DOCUMENTS

| | | | | |
|---|---|---|---|---|
| 2004/0252870 | A1* | 12/2004 | Reeves | G06T 7/0012 |
| | | | | 382/128 |
| 2008/0058593 | A1* | 3/2008 | Gu | G06T 5/006 |
| | | | | 600/109 |
| 2008/0205717 | A1* | 8/2008 | Reeves | G06T 5/002 |
| | | | | 382/128 |
| 2009/0063431 | A1* | 3/2009 | Erol | G06K 9/6293 |
| 2009/0141932 | A1* | 6/2009 | Jones | G06K 9/036 |
| | | | | 382/100 |
| 2011/0075914 | A1* | 3/2011 | Filkins | G06T 7/0002 |
| | | | | 382/133 |
| 2014/0378810 | A1* | 12/2014 | Davis | A61B 5/1034 |
| | | | | 600/407 |
| 2016/0247034 | A1* | 8/2016 | Lee | G06K 9/00684 |
| 2018/0144214 | A1* | 5/2018 | Hsieh | G06N 3/08 |

* cited by examiner

METHOD AND DEVICE FOR THE AUTOMATED EVALUATION OF AT LEAST ONE IMAGE DATA RECORD RECORDED WITH A MEDICAL IMAGE RECORDING DEVICE, COMPUTER PROGRAM AND ELECTRONICALLY READABLE DATA CARRIER

PRIORITY STATEMENT

The present application hereby claims priority under 35 U.S.C. § 119 to German patent application number DE 102017221297.7 filed Nov. 28, 2017, the entire contents of which are hereby incorporated herein by reference.

FIELD

Embodiments of the invention generally relate to a method for the automated evaluation of at least one image data record of a patient recorded with a medical image recording device for the preparation of diagnostic findings, a corresponding device, a computer program and an electronically readable data carrier.

BACKGROUND

Various types of medical imaging techniques permit an ever more precise insight into the anatomy of patients. Nonetheless, the evaluation of such image data records, in particular with regard to a diagnostic finding, proves to be an extremely challenging and difficult task for which the quality of the medical image data record of the patient is highly relevant. It is current practice to employ sophisticated manual evaluation and diagnostic finding processes to derive clinically relevant results from a medical image data record, wherein specialized evaluation algorithms which can support the corresponding diagnostician have been proposed for subtasks. The mainly manual, operator-assessed approach has its drawbacks.

With regard to the quality of the final clinical evaluation results, there is a dependence on the quality of the preceding evaluation steps, wherein this quality concerns both the quality of the recorded medical image data record and the quality of the editing and/or preparation for diagnosis. In this case, preparation for diagnosis may also include a multiplicity of manual measures, for example, editing measures taken by the technician and annotations/reports from radiologists. Current practice is therefore based on a largely manual workflow which is subject to human error, not standardized between different institutions and produces evaluation results which cannot be reproduced.

Another problem arises in terms of efficiency. Due to the intensive, manual work required, some clinical results cannot be obtained with the necessary and/or desired speed, for example, in medical emergencies such as acute trauma. Furthermore, depending on the respective installation and regional requirements, the costs associated with the production of clinical evaluation processes may possibly not be justified and/or adequately covered by reimbursement models. Thus, for example, three-dimensional imaging is not reimbursed in many countries. Some clinical evaluation results require a high degree of specialization, placing high demands and restrictions on the recruitment and retention of medical personnel, for example, with regard to cardiac imaging.

Finally, the clinical findings are a further concern. Some clinical evaluation results require a highly complex and precise cognitive process which can only be realized with great difficulty by many people, for example, when evaluating the risk of a coronary lesion. Such clinical findings, which directly affect patient management, usually require further sources of additional information which have been previously determined and/or are to be determined to support decision-making. Obtaining and incorporating this data for improved prediction is challenging, especially in a manual workflow.

In conclusion, obtaining clinical results is a complex, manual process involving a multiplicity of specialists and varying greatly between institutions and geographically. The process can comprise the following steps: scanning of the patient and generation of image data records, editing of image data records and preparation of the image results (manually performed by a technician at the recording location or outsourced), obtaining findings from and interpreting of image results (manually performed by a radiologist, again either at the recording location or outsourced), generation of clinical results, in particular of a report, derived result data records and/or quantitative results (again manually by a radiologist or outsourced), review of the clinical findings by a more senior radiologist and reference to examination results of a doctor and diagnosis/determination of further measures.

SUMMARY

At least one embodiment of the invention specifies an improved approach permitting further automation for generating clinical evaluation results as the basis for a finding.

According to at least one embodiment of the invention, a method is provided in which at least one item of input data describing the patient and/or the recording process and/or the examination target is determined after completion of the recording of the image data record, wherein a selection algorithm evaluating the image data record and the input data is used to determine at least one automated evaluation process to be applied and applicable and through evaluation of the image data record at least one image quality measure with regard to the evaluation process is determined, wherein the selected automated evaluation process is only performed for an image quality measure meeting a minimum quality requirement.

At least one embodiment of the present invention also relates to a method for automated evaluation of at least one image data record of a patient, recorded with a medical image recording device, for the preparation of diagnostic findings, the method comprising:

determining, after recording of the at least one image data record, at least one item of input data describing at least one of the patient, a recording process and an examination target, the determining including
  using a selection algorithm, evaluating the at least one image data record and the at least one item of input data, to select at least one automated evaluation process to be applied and applicable, and
  determining, through evaluation of the at least one image data record, at least one image quality measure with regard to the at least one automated evaluation process, wherein the at least one automated evaluation process selected is only performed for an image quality meeting a threshold quality requirement.

In addition to the method, at least one embodiment of the present invention also relates to a device for the automated evaluation of at least one image data record of a patient recorded with a medical image recording device in order to prepare a diagnosis, having at least one computing device designed to carry out the method according to at least one embodiment of the invention. All the embodiments with regard to the method according to at least one embodiment of the invention can be applied analogously to the device according to at least one embodiment of the invention with which the aforementioned advantages can thus also be obtained.

The computing device may have a processor and/or a storage device. Specifically, the computing device may have a selection unit for selecting automated evaluation processes to be performed, an image quality unit for determining the image quality measure, an execution unit for carrying out the selected automated evaluation processes, and in particular, also an output unit that, for example, can control an output device in order to output evaluation results. Optional additional units are a landmark unit for determining landmark information and particularly preferably, an evaluation quality unit for determining the evaluation quality measure. With regard to an output device and/or an output unit, it should also be noted that the at least one evaluation result can by all means be output, for example, on a monitor or the like, but it is also possible to add and/or to assign the evaluation result to the image data record and to save the supplemented image data record and/or the supplements, for example, in an image archiving system (PACS) for subsequent evaluation. If the image data record is available in DICOM format, for example, freely available portions of the metadata can be used for recording evaluation results. The final diagnosis can then be carried out at a diagnostic findings workstation or the like.

A computer program according to at least one embodiment of the invention can, for example, be loaded directly into a memory of a computing device of a device according to at least one embodiment of the invention and has program resources to perform the steps of a method described herein when the computer program is executed in the computing device. The computer program can be saved on an electronically readable data carrier according to at least one embodiment of the invention which thus comprises electronically readable control information stored thereon comprising at least one computer program according to at least one embodiment of the invention and designed such that when the data carrier is used in a computing device of a device according to at least one embodiment of the invention, it performs a method described herein. The data carrier is preferably a non-transient data carrier, for example, a CD-ROM.

At least one embodiment of the present invention also relates to a device for automated evaluation of at least one image data record of a patient recorded with a medical image recording device for preparation of diagnostic findings, comprising:
  at least one computing device, designed to
  determine, after recording of the at least one image data record, at least one item of input data describing at least one of the patient, a recording process and an examination target, the determining including
    use a selection algorithm, evaluating the at least one image data record and the at least one item of input data, to select at least one automated evaluation process to be applied and applicable, and
    determine, through evaluation of the at least one image data record, at least one image quality measure with regard to the at least one automated evaluation process, wherein the at least one automated evaluation process selected is only performed for an image quality meeting a threshold quality requirement.

At least one embodiment of the present invention also relates to a memory storing a computer program, including a set of instructions which, when executed by at least one computing device, cause the at least one computing device to perform a method for automated evaluation of at least one image data record of a patient, recorded with a medical image recording device, for the preparation of diagnostic findings, the method comprising:
  determining, after recording of the at least one image data record, at least one item of input data describing at least one of the patient, a recording process and an examination target, the determining including
    using a selection algorithm, evaluating the at least one image data record and the at least one item of input data, to select at least one automated evaluation process to be applied and applicable, and
    determining, through evaluation of the at least one image data record, at least one image quality measure with regard to the at least one automated evaluation process, wherein the at least one automated evaluation process selected is only performed for an image quality meeting a threshold quality requirement.

BRIEF DESCRIPTION OF THE DRAWINGS

Further advantages and details of the present invention will emerge from the example embodiments described hereinafter and with reference to the drawing. The diagrams show.

DETAILED DESCRIPTION OF EXAMPLE EMBODIMENTS

Figure 1:
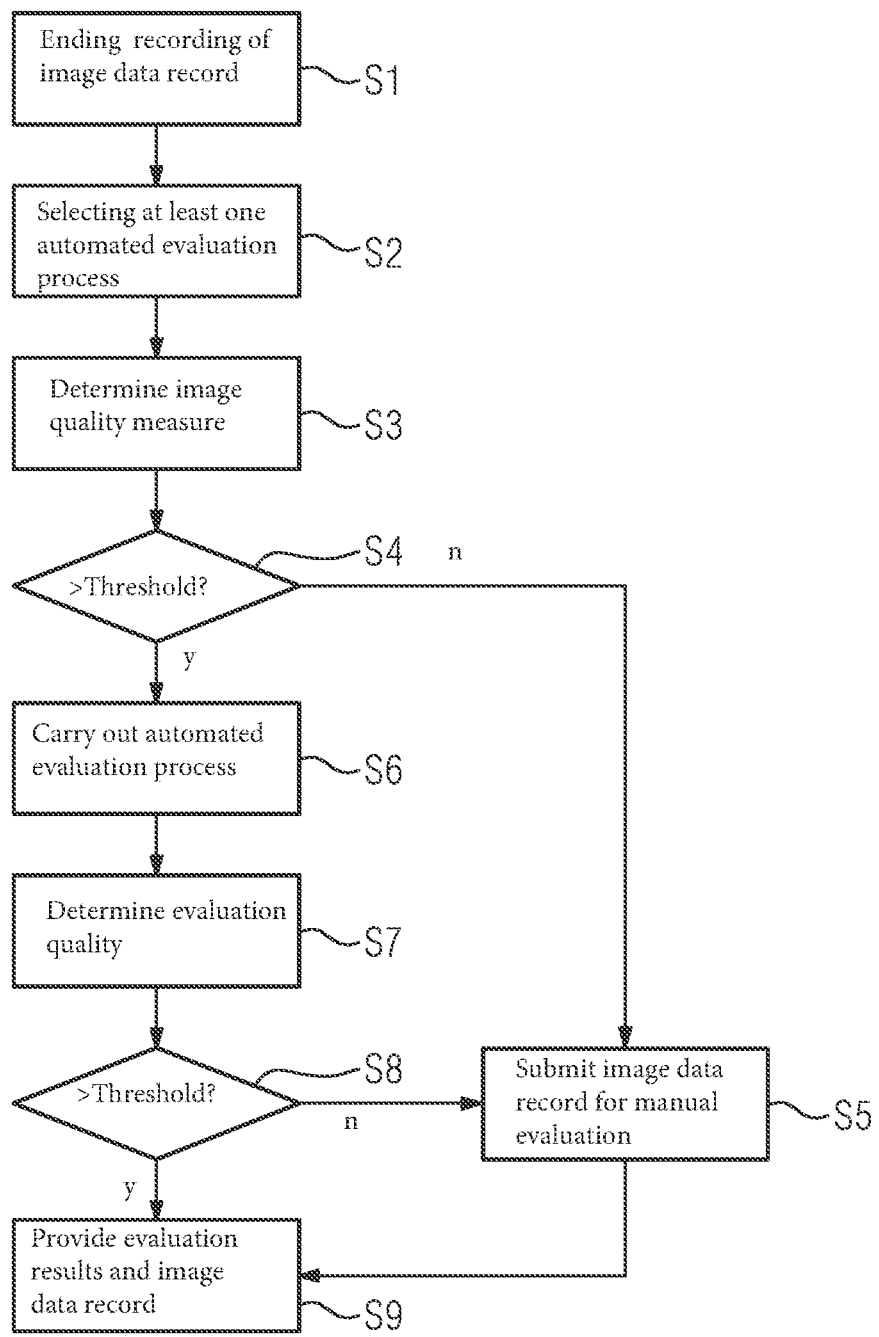
FIG. 1 A flow chart of an example embodiment of the method according to the invention, and FIG. 2 A device according to an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

According to at least one embodiment of the invention, a method is provided in which at least one item of input data describing the patient and/or the recording process and/or the examination target is determined after completion of the recording of the image data record, wherein a selection algorithm evaluating the image data record and the input data is used to determine at least one automated evaluation process to be applied and applicable and through evaluation of the image data record at least one image quality measure with regard to the evaluation process is determined, wherein the selected automated evaluation process is only performed for an image quality measure meeting a minimum quality requirement.

According to at least one embodiment of the invention, it is proposed that a selection algorithm which is preferably an algorithm of artificial intelligence is first used in order to conclude in an automated manner which results of the image data record are required for the following diagnostic finding, are therefore to be determined, are available for the automated evaluation processes, in particular, evaluation algorithms realized as program resources.

However, before the automated evaluation processes which were selected are performed, the quality of the image data record is assessed in terms of this automated evaluation process, the extent to which the image data record is suitable for providing sufficiently accurate and/or reliable evaluation results when employing at least one selected automated evaluation process is thus determined. In this case too, recent technological advances with regard to artificial intelligence, which will be discussed in more detail below, can preferably be used. Only when an image quality measure is available in relation to at least one selected evaluation process that falls below a certain threshold value for the image quality measure is the image data record removed and forwarded for manual further processing. Otherwise, the corresponding at least one selected evaluation process is performed automatically and produces corresponding evaluation results.

Overall, it is therefore possible to automatically generate clinical evaluation results as the basis for a diagnostic finding immediately after completion of the recording and generation of the image data record in a fully automated manner, without the need for interaction with a user. The actual final assessment, in particular, diagnosis, will continue to be performed by a physician based on the evaluation results.

At least one embodiment of the present invention therefore permits the generation of clinical evaluation results with improved quality, an increased degree of standardized reproducibility, efficiency, speed, reduced costs, reduced personnel specialization requirements, increased predictive value and with a lower level of complexity. The automated evaluation of medical image data records therefore permits improved standardization and the acceleration of corresponding workflows, wherein in addition, especially due to the examination of the image quality measure, an improved guarantee of the image quality and therefore evaluation result quality is enabled. Patient management and clinical treatment results are improved.

The input data can be automatically obtained in various ways. The input data can preferably be retrieved from an information system and/or an electronic patient file and/or from the image recording device. After, for example, a patient is customarily captured by way of data processing before image recording, useful patient data may already be accessible as input data by way of a computing device carrying out the method. An electronic patient file which, for example, can be stored in a corresponding database, proves to be a particularly useful source of patient information and examination target information. Information about the recording procedure can, for example, be obtained from the medical image recording device itself, which is particularly advantageous if the method is performed directly on the medical image recording device. Information systems which can provide further information are, for example, hospital information systems (HIS) and/or radiology information systems (RIS).

Specifically, it can be provided that at least one item of patient data describing the patient and/or at least one item of image information describing the image content and/or at least one recording parameter used for recording the image data record and/or at least one result of a previous examination of the patient are used as input data. In addition to the image data record itself, hence the corresponding image data, the input data may therefore also comprise patient data, for example, data from an electronic patient file, information about the recording parameters with which the image data record was recorded, information relating to the aim of the image recording, for example, from a referral or the like, and recently received clinical information about the patient.

In a particularly advantageous embodiment of the present invention, it can be provided that before the application of the selection algorithm, a whole-body landmark detection algorithm is used to detect anatomical features shown within the image data record, the landmark information of which, obtained as a result, is used as input data, in particular, image content data. Pre-processing can therefore be provided in which an available landmark algorithm is used to detect landmarks which, in particular, is suitable for all areas of the human body in order to detect anatomical landmarks, therefore anatomical features, available in the image data record. In particular, the landmark algorithm may in turn preferably be an algorithm of artificial intelligence after corresponding landmark algorithms were already proposed in the prior art.

In this context, it is expedient if the landmark information is used to restrict the scope of applicable automated evaluation processes. Such a pre-processing step therefore provides information on the basis of which the body regions which can be analyzed in more detail by automated evaluation processes can already be restricted so that a corresponding reduction in the possible range of results can be undertaken, allowing the selection algorithm to be carried out in a manner involving less time and/or requiring less computing power. As aforementioned, it is particularly preferred if the selection algorithm is an algorithm of artificial intelligence which, in particular, is trained by way of a deep learning method.

As has already been explained, at least one embodiment of the present invention thus uses recent technical advances with regard to artificial intelligence, wherein deep learning approaches are particularly preferably used to enable the automatic processing of clinical image data described here, in particular immediately after recording. New algorithms of artificial intelligence, as proposed in the prior art, enable even extremely complex combination patterns to be detected in an effective, sufficiently fast manner, in particular even complex input data, such as the image data record in the present case, to be processed and robust, reliable results to be generated. This can also be used, in particular with regard to the image quality measure which is to be provided in relation to automated evaluation processes to be carried out.

Accordingly, a preferred embodiment of the present invention provides that the image quality measure is determined by way of an image quality algorithm of artificial intelligence. In this case, it is in turn particularly preferred if the image quality algorithm is trained by way of training data, in particular using a deep learning method, wherein the training data may comprise a basic truth provided by at least one expert. Particularly preferably in this context, a neural network is used as an image quality algorithm of artificial intelligence which is trained by way of deep learning in order to obtain a quantitative image quality measure, wherein the corresponding input data of the image quality algorithm of artificial intelligence can at least partially describe and/or comprise the image data record itself and the corresponding automated evaluation processes to be carried out.

Furthermore, it is particularly preferred if, in order to determine the image quality measure, first image quality data is determined from the image data of the image data record which is used in particular as input data of the image quality algorithm of artificial intelligence. The image information itself, which is contained in the image data of the image data record, is therefore used to provide indications which are already useful and on the basis of which the quality with regard to at least one automated recording process for performance can be assessed.

Specifically, it can be provided that a physically based basic measure, in particular a signal-to-noise ratio and/or a contrast-to-noise ratio and/or an image resolution, and/or an image content measure which is determined in particular as a function of landmark information and/or a segmentation result of a preceding segmentation, and/or an artifact measure describing the existence and/or strength of image artifacts and/or motion artifacts in the image data record and/or an item of image content information derived in particular from landmark information and/or at least already partially used as input data, which describes the presence and/or absence of at least one anatomical feature, are determined as image quality data.

The image quality measure, which can also be referred to as the "Image Quality Score", can therefore first use conventional, physically-based measures, for example, the signal-to-noise ratio (SNR), the contrast-to-noise ratio (CNR), the pixel resolution and/or the layer thickness and the like. Furthermore, derived, image-based measures can be used, for example, the contrast level and the contrast homogeneity inside recorded blood vessels and the like.

Further image-based measures, which can be used appropriately, measure the existence and frequency of known image artifacts, for example, streak artifacts and/or so-called blooming artifacts. Algorithms for the detection of such image artifacts have already been proposed in the prior art, in particular with regard to their correction, which can also be used in the context of at least one embodiment of the present invention. This applies accordingly to the use of image-based methods to assess the existence and strength of motion artifacts and to determine a corresponding artifact measure. The landmark information already mentioned, in particular combined with registration and/or segmentation approaches, can be used particularly advantageously to determine which anatomical features are contained in the image data record and which are missing so that, for example, it can be established whether anatomical features which should actually be analyzed by the automated process are not present or the like.

In summary, an "Image Quality Score" is therefore determined as an image quality measure by way of a preferred intelligent quality algorithm in order to objectify the quality of the image data record with regard to the evaluation processes to be performed, wherein this image quality measure is used together with a predetermined threshold value to exclude image data records with inferior image quality from further automated processing.

Possible program resources realizing automated evaluation processes can be stored in a database and/or a software library and/or provided as cloud services in order to ensure corresponding access to a sufficient quantity of automated evaluation processes. Specifically, it is possible to use as evaluation processes those which output as an evaluation result a modified result data record determined from the image data record or, in particular by way of annotation, and/or quantitative evaluation information, in particular a clinical score, and/or a classification and/or textual report modules.

In the prior art, a multiplicity of possible automated evaluation processes were already proposed, for example, in relation to perfusion in the brain, the analysis of strokes, for evaluating dual energy image data, for detecting ribs, for superimposing three-dimensional image data records, for blood vessel analysis, for coronary analysis, for determining calcium scores, for analyzing filling defects in contrast agent imaging, for computer-aided diagnosis (CAD), for example of the lung and/or the intestine, for detecting polyps in the rectum, and the like. Evaluation results can receive images as result data records, for example, MPR, CPR, VRT, MIP, cinematically rendered images and the like.

Quantitative evaluation results may contain measurements within the imaged body region, for example, of illustrated anatomical features, for example, of the length, the volume, the diameter, the number of stenoses, various ratios and the like. Measurements that can be carried out automatically, such as the determination of FFR values (Fractional Flow Reserve), wall shear stress values and the like are also possible. Predictive results include, for example, risk scores, such as those which have already been defined in the prior art in various ways, for example MACE (Major Adverse Cardiac Events), risks involving the tearing of a brain aneurysm and the like. Report evaluation results are also conceivable, for example containing formulations of certain interpretations which can be used directly or indirectly in a final diagnosis report.

In a particularly preferred embodiment of the present invention, it can be provided that an evaluation quality measure is determined for the evaluation result of at least one executed automated evaluation process, wherein in the case of a second minimum quality requirement, the evaluation result is discarded and the image data record is submitted for manual processing. Within such a step, the plausibility and quality of the evaluation results are evaluated and reproduced quantitatively in the form of a "Result Quality Score". If the evaluation quality measure does not exceed a certain second threshold value, the corresponding case is diverted for manual processing. However, if the second minimum quality requirement is met, the evaluation results can be compiled and submitted for clinical assessment. In this way, the quality of the preparation of the image data record providing automatic evaluation results for diagnosis is further improved and/or high quality is ensured.

Expediently, the evaluation quality measure and/or an item of evaluation quality data for determining the evaluation quality measure can be output as reliability information by an evaluation algorithm implementing the automated evaluation process. Modern algorithms which implement automated evaluation processes usually already provide a statement about how reliable the evaluation result is, for example, error and/or tolerance values and the like. These values can usefully be included in the evaluation quality measure, in particular as input data (evaluation quality data).

For in a particularly advantageous manner, it can be provided within the scope of the invention that the evaluation quality measure is determined by way of an evaluation quality algorithm of artificial intelligence. Here, too, for example, as in all mentioned algorithms of artificial intelligence, neural networks or the like can be used, wherein a deep learning method is preferably used for training. A basic truth in training data for the evaluation algorithm can often be derived from further observation of a patient as it often emerges over time whether certain circumstances described by the evaluation results are in fact present and the like.

In an expedient development, the evaluation quality measure can be determined by taking into account the complexity information describing the physical complexity of the patient-specific anatomy and/or morphology and/or physiology and/or background information describing pathologies diagnosed and/or to be diagnosed and/or previous medical interventions. Furthermore, it is expedient to use a priori information describing the plausibility and/or the variation of at least part of the evaluation results. Thus, for example, a measure of complexity can be used which describes the physical complexity of the intrinsic patient-specific anatomy, morphology and physiology.

Examples of such measures of complexity and/or complexity information are the number of branches of the coronary arteries, the number and topology of the pulmonary arteries, the size, position and shape of certain anatomical features and the like. Background information, however, is information about known pathologies and the medical history of the patient, such as can be retrieved, for example, together with other patient data from corresponding databases/an electronic patient file and/or can be derived directly from the available image data records. Examples thereof are the presence of a sternotomy, the existence of a bypass, the removal of a kidney, a calcified vascular system, the presence of aneurysms and the like. In this case, a priori information can also refer to this complexity information and/or background information, in particular if additional information influencing the evaluation results in a positive or negative manner is known.

For example, it is known that in known topologies of anatomical features a greater risk and/or more complex clinical symptoms exist, wherein the corresponding knowledge can be worked out from the population. For example, it is therefore conceivable to use prevalence for the presence of certain morphologies or the like. If, for example, it is known that by virtue of the complexity information for anatomical features, an automated evaluation process is significantly more difficult and/or is significantly more susceptible to errors, a corresponding reduction of the evaluation quality measure can be undertaken. This also applies with regard to other aggravating circumstances, for example if the background information contains an indication that a bypass is already present, making automated evaluation processes and/or also predictive measures and the like more difficult.

A specific, preferred embodiment therefore provides that for the complexity information and/or the background information, prevalence information describing the prevalence of a health anomaly to be assessed with regard to the respective information is taken into account.

In addition to the method, at least one embodiment of the present invention also relates to a device for the automated evaluation of at least one image data record of a patient recorded with a medical image recording device in order to prepare a diagnosis, having at least one computing device designed to carry out the method according to at least one embodiment of the invention. All the embodiments with regard to the method according to at least one embodiment of the invention can be applied analogously to the device according to at least one embodiment of the invention with which the aforementioned advantages can thus also be obtained.

The computing device may have a processor and/or a storage device. Specifically, the computing device may have a selection unit for selecting automated evaluation processes to be performed, an image quality unit for determining the image quality measure, an execution unit for carrying out the selected automated evaluation processes, and in particular, also an output unit that, for example, can control an output device in order to output evaluation results. Optional additional units are a landmark unit for determining landmark information and particularly preferably, an evaluation quality unit for determining the evaluation quality measure. With regard to an output device and/or an output unit, it should also be noted that the at least one evaluation result can by all means be output, for example, on a monitor or the like, but it is also possible to add and/or to assign the evaluation result to the image data record and to save the supplemented image data record and/or the supplements, for example, in an image archiving system (PACS) for subsequent evaluation. If the image data record is available in DICOM format, for example, freely available portions of the metadata can be used for recording evaluation results. The final diagnosis can then be carried out at a diagnostic findings workstation or the like.

A computer program according to at least one embodiment of the invention can, for example, be loaded directly into a memory of a computing device of a device according to at least one embodiment of the invention and has program resources to perform the steps of a method described herein when the computer program is executed in the computing device. The computer program can be saved on an electronically readable data carrier according to at least one embodiment of the invention which thus comprises electronically readable control information stored thereon comprising at least one computer program according to at least one embodiment of the invention and designed such that when the data carrier is used in a computing device of a device according to at least one embodiment of the invention, it performs a method described herein. The data carrier is preferably a non-transient data carrier, for example, a CD-ROM.

FIG. 1 shows a flow chart of an example embodiment of the method according to the invention as performed, for example, in a device according to the invention, which can also be integrated into an image recording device. In a step S1, the recording of an image data record of a patient has just ended.

As a result, in a step S2 at least one automated evaluation process is selected automatically by way of a selection algorithm of artificial intelligence, by which the image data record is evaluated in order to generate evaluation results which are useful for the assessment. An intelligent selection algorithm is therefore used to determine the kind of clinical results which can be derived from the image data record of the patient.

In addition to the image data record itself, the selection algorithm can use any type of patient data as input data, for example, from an electronic patient file, information about the recording parameters, information with regard to the examination target, information about recent clinical results of the patient and the like. These can, for example, be retrieved from information systems, from the image recording device and/or other connected computing devices. Before the selection algorithm is used, a landmark algorithm of artificial intelligence which is suitable for detecting anatomical features as landmarks for all possible areas of the human body is first used. Landmark information which corresponds to image content information and is likewise used as input data is obtained as a result of this landmark algorithm. The landmark information is used in order to limit the number of possible automated evaluation processes.

The selection algorithm of artificial intelligence, which is trained by way of a deep learning method, supplies a list of applicable automated evaluation processes for the image data record of the patient as output data which has been determined from a predefined complete list of possible automated evaluation processes, possibly limited due to the landmark information.

In a step S3, an image quality measure for the image data record is then determined based on the application, that is, based on the at least one automated, selected evaluation process. In other words, in step S3 an image quality algorithm of artificial intelligence is used to calculate an image quality measure that objectives the quality of the image data record. In a step S4, this "score" is compared to a first predetermined threshold value to establish whether the quality of the image data record is good enough to undertake an automated evaluation.

The image quality algorithm uses input data which is partially determined by preprocessing from the image data record. This includes conventional physical-based measures such as SNR, CNR, image resolution and the like, derived image-based measures, artifact measures describing image artifacts and motion artifacts in number and strength, and the like. The landmark information of step S2, optionally supplemented by registration and/or segmentation results, is also used to determine what is depicted in the image data record and what is missing in the image data record.

If in step S4 it emerges that the image quality measure is smaller than the first threshold value, the image data record is not evaluated by the selected automated evaluation processes in an automated manner, but is transferred for manual processing in step S5. If the first minimum quality requirement described by the first threshold value is met, however, the selected automated evaluation processes are carried out in a step S6, wherein corresponding evaluation algorithms implemented as a computer program including program segments/modules, which can also comprise evaluation algorithms of artificial intelligence, are used. Depending on the evaluation process, different types of evaluation results can be generated, comprising images (result data records), quantitative results such as scores, predictive values, measurements carried out in the image data record, pre-formulated report parts and the like. A multiplicity of such aids is known in the prior art.

In a step S7 an intelligent evaluation quality algorithm is used in order to determine an evaluation quality measure describing the plausibility and quality of the evaluation results of step S5.

If it is then determined in a step S8 that a second threshold value has not been reached, the image data record is in turn submitted for manual evaluation to check or to discard the evaluation results in step S5; if the second threshold value, which describes a second minimum quality requirement, is exceeded, however, the evaluation results and the image data record are provided for diagnosis in step S9.

On the one hand, the evaluation quality algorithm of artificial intelligence in particular uses reliability information provided by evaluation algorithms themselves, but on the other hand, also at least one item of complexity information and at least one item of background information. The complexity information describes the physical complexity of the intrinsic patient-specific anatomy, morphology and physiology, the background information describes known pathologies and the medical history of the patient, after both the complexity of the anatomy per se and previous interventions/changes complicate or in some cases simplify the automated evaluation, which is reflected accordingly in the evaluation quality measure. In particular, therefore, a priori existing medical and technical knowledge is introduced, for example as prevalence information, into the determination of the evaluation quality measure in order to make the quality inspection implemented thereby more reliable. Further evaluation quality information used by the evaluation quality algorithm of artificial intelligence may comprise a priori information about the plausibility of the results, based on the known variance, in particular for the population of the patient.

In step S9 the evaluation results are output, wherein these can be added to the image data record or can be assigned to it, wherein the image data record supplemented in this way and/or the supplements can then be stored in an image archiving system (PACS) and/or directly output, for example, on a diagnostic workstation. It should be noted that if the minimum quality requirements of steps S4 and S8 have not been satisfied, the results of individual manual findings in step S5 can also naturally, as is known in principle, be saved in an image archiving system and the like again.

Figure 2:
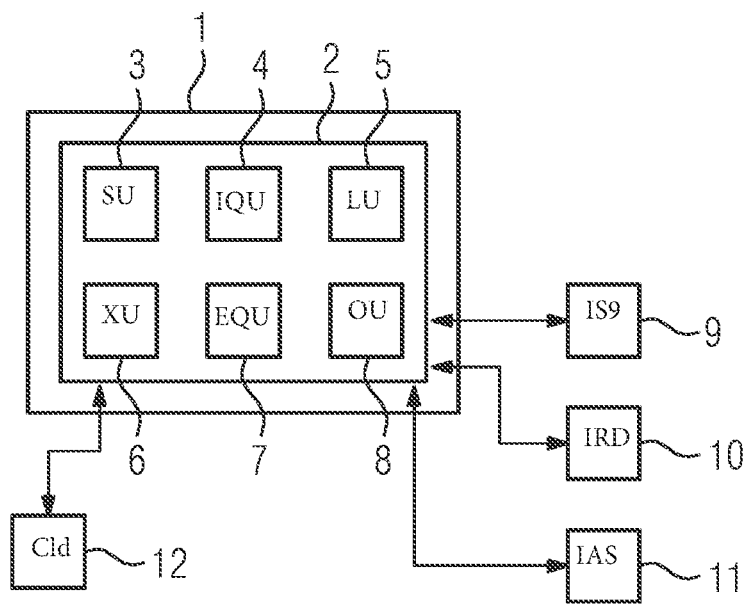

Finally, FIG. 2 shows a schematic diagram of a device 1 according to the invention for the automated evaluation of an image data record of a patient. This comprises a computing device 2 which is designed to carry out the method described with regard to FIG. 1. For this purpose, the computing device 2 in the present case comprises a selection unit 3 for selecting the process to be automated, an image quality unit 4 for determining the image quality measure, a landmark unit 5 for determining the landmark information, an execution unit 6 for carrying out the automated evaluation processes, an evaluation quality unit 7 for determining the evaluation quality measure and an output unit 8 for outputting the results.

The computing device 2 can be connected via corresponding communication connections to at least one information system 9 in which, for example, electronic patient files can be stored, and/or to the image recording device 10 and/or to an image archiving system 11.

It should be noted that the device 1 can in particular also be realized as part of a medical image recording device 10.

Finally, it is conceivable that the computing device 2 also communicates with a cloud 12, wherein at least parts of the automated evaluation processes can be provided as cloud services.

Although the invention has been illustrated and described in more detail by the preferred example embodiment, the invention is not restricted by the disclosed examples and other variations can be derived from it by a person skilled in the art, without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for deciding whether to perform automated evaluation of morphological features of at least one image data record of a patient, recorded with a medical image recording device, for preparation of diagnostic findings, the method comprising:
   determining, after recording of the at least one image data record, at least one item of input data describing at least one of the patient, a recording process, and an examination target, the determining including,
      using a selection algorithm, pre-evaluating the at least one image data record and the at least one item of input data, to select at least one automated evaluation process of the morphological features to be applied, and
      determining, based on the pre-evaluating of the at least one image data record, at least one image quality measure associated with the at least one automated evaluation process of the morphological features, the at least one image quality measure being based on a complexity of the morphological features, wherein
   the at least one automated evaluation process of the morphological features selected is only performed on the at least one image data record in response to the at least one image quality measure meeting a threshold quality requirement, wherein
   the complexity of the morphological features include at least one of a number of branches of coronary arteries, a number of pulmonary arteries, or a topology of the pulmonary arteries.

2. The method of claim 1, wherein at least one of
   the at least one item of input data is retrieved from at least of an information system, an electronic patient file, and the medical image recording device,
   at least one item of patient data describing the patient is used as the at least one item of input data,
   at least one item of image content information describing image contents of the image data record is used as the at least one item of input data,
   at least one recording parameter used for recording the image data record is used as the at least one item of input data, and
   at least one result of a previous examination of the patient is used as the at least one item of input data.

3. The method of claim 2, wherein the at least one item of input data includes landmark information of anatomical features obtained before the using of the selection algorithm by a whole-body landmark detection algorithm, that detects anatomical features shown within the at least one image data record.

4. The method of claim 2, wherein, the determining the at least one image quality measure includes determining first image quality data derived from image data of the at least one image data record.

5. The method of claim 2, further comprising: determining an evaluation quality measure for the evaluation result of the at least one automated evaluation process executed;
   discarding the evaluation result; and
   submitting the at least one image data record is submitted for manual processing upon the evaluation quality measure not satisfying a second threshold quality requirement.

6. A non-transitory electronically readable data carrier storing a computer program, including a set of instructions which, when executed by a computing device, cause the computing device to perform the method of claim 2.

7. The method of claim 5, further comprising at least one of:
outputting at least one of the evaluation quality measure and an item of evaluation quality data for determining the evaluation quality measure as an item of reliability information from an evaluation algorithm realizing the at least one automated evaluation process; and
determining the evaluation quality measure through an evaluation quality algorithm of artificial intelligence.

8. The method of claim 5, wherein the determining the evaluation quality measure includes taking into account complexity information describing physical complexity of at least one of patient-specific anatomy, patient-specific morphology, patient-specific physiology, background information describing a pathology diagnosed or to be diagnosed, previous medical interventions, a priori information describing plausibility and a variation of at least part of the evaluation result.

9. The method of claim 7, wherein the determining the evaluation quality measure includes taking into account complexity information describing physical complexity of at least one of patient-specific anatomy, patient-specific morphology, patient-specific physiology, background information describing a pathology diagnosed or to be diagnosed, previous medical interventions, a priori information describing plausibility and a variation of at least part of the evaluation result.

10. The method of claim 1, wherein, the at least one item of input data includes landmark information of anatomical features, the anatomical features being obtained before the using of the selection algorithm by a whole-body landmark detection algorithm that detects the anatomical features within the at least one image data record.

11. The method of claim 10, wherein the selection algorithm is an algorithm of artificial intelligence, trained via a deep learning method.

12. The method of claim 1, wherein the selection algorithm includes an algorithm of artificial intelligence, trained via a deep learning method.

13. The method of claim 1, wherein, the determining the at least one image quality measure includes determining first image quality data, derived from image data of the at least one image data record.

14. The method as claimed in claim 13, wherein the first image quality data includes a physically based basic measure determined as a function of at least one of at least one of landmark information and a segmentation result of a preceding segmentation.

15. The method of claim 14, wherein the physically based basic measure includes at least one of a signal-to-noise ratio, a contrast-to-noise ratio, an image resolution, and an image content measure.

16. The method of claim 14, wherein the physically based basic measure includes at least one of
(a) an artifact measure describing at least one of existence and strength of at least one of image artifacts and motion artifacts in the at least one image data record,
(b) image content information derived from landmark information, and
(c) image content information at least already partially used as the at least one item of input data, which describes at least one of presence and absence of at least one anatomical feature.

17. The method of claim 1, wherein the determining the at least one image quality measure includes determining the at least one image quality measure by way of an image quality algorithm of artificial intelligence.

18. The method of claim 1, wherein program resources to implement the at least one automated evaluation process are at least one of
(a) stored in at least one of a database and software library,
(b) provided as cloud services,
(c) determined from the at least one image data record, or
(d) at least one item of quantitative evaluation information.

19. The method of claim 1, further comprising:
determining an evaluation quality measure for an evaluation result of the at least one automated evaluation process executed;
discarding the evaluation result; and
submitting the at least one image data record for manual processing upon the evaluation quality measure not satisfying a second threshold quality requirement.

20. The method of claim 19, wherein the method further comprises at least one of
outputting at least one of the evaluation quality measure and an item of evaluation quality data for determining the evaluation quality measure as an item of reliability information from an evaluation algorithm realizing the at least one automated evaluation process, and
determining the evaluation quality measure through an evaluation quality algorithm of artificial intelligence.

21. The method of claim 19, wherein the determining the evaluation quality measure includes taking into account complexity information describing physical complexity of at least one of patient-specific anatomy, patient-specific morphology, patient-specific physiology, background information describing a pathology diagnosed or to be diagnosed, previous medical interventions, a priori information describing plausibility and a variation of at least part of the evaluation result.

22. The method of claim 20, wherein the determining the evaluation quality measure includes taking into account complexity information describing physical complexity of at least one of patient-specific anatomy, patient-specific morphology, patient-specific physiology, background information describing a pathology diagnosed or to be diagnosed, previous medical interventions, a priori information describing plausibility and a variation of at least part of the evaluation result.

23. The method of claim 21, wherein at least one of the complexity information or the background information includes prevalence information describing prevalence of a health anomaly to be assessed in relation to respective information.

24. A non-transitory electronically readable data carrier storing a computer program, including a set of instructions which, when executed by a computing device, cause the computing device to perform the method of claim 1.

25. A device for deciding whether to perform automated evaluation of morphological features of at least one image data record of a patient recorded with a medical image recording device for preparation of diagnostic findings, comprising:
at least one computing device, configured to execute machine-readable instructions that, when executed by the at least one computing device, cause the device for automated evaluation to
determine, after recording of the at least one image data record, at least one item of input data describing at least one of the patient, a recording process, and an examination target, the determining including use a selection algorithm, pre-evaluating the at least one image data record and the at least one item of input data, to select at least one automated evaluation process of the morphological features to be applied, and determine, based on the pre-evaluating of the at least one image data record, at least one image quality measure associated with at least one automated evaluation process of the morphological features, the at least one image quality measure being based on a complexity of the morphological features, wherein the at least one automated evaluation process selected is only performed on the at least one image data record in response to the at least one image quality measure meeting a threshold quality requirement, wherein the complexity of the morphological features include at least one of a number of branches of coronary arteries, a number of pulmonary arteries, or a topology of the pulmonary arteries.

26. A memory storing a computer program, including a set of instructions which, when executed by at least one computing device, cause the at least one computing device to decide whether to perform a method for automated evaluation of morphological features of at least one image data record of a patient, recorded with a medical image recording device, for preparation of diagnostic findings, the method comprising:

determining, after recording of the at least one image data record, at least one item of input data describing at least one of the patient, a recording process, and an examination target, the determining including using a selection algorithm, pre-evaluating the at least one image data record and the at least one item of input data, to select at least one automated evaluation process of the morphological features to be applied, and determining, based on the pre-evaluating of the at least one image data record, at least one image quality measure associated with at least one automated evaluation process, the at least one image quality measure being based on a complexity of the morphological features, wherein the at least one automated evaluation process of the morphological features selected is only performed on the at least one image data record in response to the at least one image quality measure meeting a threshold quality requirement, wherein the complexity of the morphological features include at least one of a number of branches of coronary arteries, a number of pulmonary arteries, or a topology of the pulmonary arteries.

27. A device for automated evaluation of at least one image data record of a patient recorded with a medical image recording device for preparation of diagnostic findings, comprising:

at least one computing device; and the memory of claim 26, storing the computer program, including a set of instructions which, when executed by the at least one computing device, cause the at least one computing device to perform the method for automated evaluation of at least one image data record of a patient, recorded with a medical image recording device, for the preparation of diagnostic findings.

\* \* \* \* \*